(12) United States Patent
Bristow et al.

(10) Patent No.: US 9,212,162 B1
(45) Date of Patent: Dec. 15, 2015

(54) PROCESS FOR THE PREPARATION OF POLYMORPHS OF IMIDACLOPRID

(71) Applicant: ROTAM AGROCHEM INTERNATIONAL COMPANY LIMITED, Chai Wan (HK)

(72) Inventors: James Timothy Bristow, Hong Kong (CN); Yifan Wu, Chai Wan (HK)

(73) Assignee: ROTAM AGROCHEM INTERNATIONAL COMPANY, LTD, Chai Wan, Hong Kong (CN)

( * ) Notice: Subject to any disclaimer, the term of this patent is extended or adjusted under 35 U.S.C. 154(b) by 0 days.

(21) Appl. No.: 14/313,632

(22) Filed: Jun. 24, 2014

(51) Int. Cl.
*C07D 401/06* (2006.01)
(52) U.S. Cl.
CPC .................................... *C07D 401/06* (2013.01)
(58) Field of Classification Search
CPC ...................................................... C07D 401/06
USPC ...................................................... 546/274.7
See application file for complete search history.

(56) References Cited

PUBLICATIONS

Kapoor et al., "Ethyl 2- etc.," Acta Cryst. (2012) E68, 0987, sup-1-sup-7.*
Kirk-Othmer Encyclopedia of Chemical Technology Copyright 2002 by John Wiley & Sons, Inc.,pp. 95-147, Article Online Posting date: Aug. 16, 2002.*

* cited by examiner

*Primary Examiner* — Patricia L Morris
(74) *Attorney, Agent, or Firm* — Dickinson Wright PLLC

(57) ABSTRACT

A process for the preparation of a Form I crystalline polymorph of imidacloprid, including: (i) dissolving imidacloprid in an appropriate amount of aqueous solvent or mixture of solvents to obtain an aqueous solution; (ii) cooling the aqueous solution slowly, thereby forming crystals of polymorph Form I of imidacloprid; (iii) isolating the crystals. A process for the preparation of a Form II crystalline polymorph of imidacloprid, comprising: dissolving imidacloprid in an appropriate amount of non-aqueous solvent or mixture of non-aqueous solvents to obtain a non-aqueous solution; (ii) cooling the solution rapidly, thereby forming crystals of polymorph Form II of imidacloprid; (iii) isolating the crystals.

8 Claims, 2 Drawing Sheets

PROCESS FOR THE PREPARATION OF POLYMORPHS OF IMIDACLOPRID

BACKGROUND

1. Field

Disclosed herein are methods for selectively producing crystal polymorphs of the compound 1-((6-Chloro-3-pyridinyl)methyl)-N-nitro-imidazolidinimine, also known as imidacloprid.

2. Description of Related Art

Solid exist in either amorphous or crystalline forms. In the case of crystalline forms, molecules are positioned in 3-dimensional lattice sites. Crystallization of solids from solution is known in the art, for example by mixing the desired compound in an appropriate amount of solvent or mixture of solvents, heating to achieve dissolution, and cooling to precipitate the product. Alternatively, the compound can be dissolved in one solvent, and a second solvent is added, until precipitation is achieved. Also, the reaction can be seeded with the appropriate compound in order to induce crystallization, as known in the art.

When a compound recrystallizes from a solution or slurry, it may crystallize with different spatial lattice arrangements, a property referred to as "polymorphism", with the different crystal forms individually being referred to as a "polymorph". Different polymorphic forms of a given substance may also differ from each other with respect to one or more physical properties, such as solubility, true density, crystal shape, compaction behavior, flow properties, and/or solid state stability.

In the case of a chemical substance that exists in two (or more) polymorphic forms having different thermodynamic stabilities, the more unstable forms generally convert to the more thermodynamically stable forms at a given temperature after a sufficient period of time. When this transformation is not rapid, the thermodynamically unstable form is referred to as the "metastable" form. In general, the stable form exhibits the highest melting point, the lowest solubility, and the maximum chemical stability of the different polymorphic forms. However, the metastable form may exhibit sufficient chemical and physical stability under normal storage conditions to permit its use in a commercial form. Furthermore, the metastable form, although less stable than the most thermodynamically stable polymorphic form, may exhibit properties that are more desirable than those of the more stable form, such as better formulative ability, improved dispersability in water, and the like.

It has been discovered that the compound imidacloprid exists in two polymorphic forms: a thermodynamically stable form, known as Form I, and a metastable form, known as Form II. The powder XRD patterns and data for the two polymorphic forms are also distinctly different. Form I exhibits an X-ray powder diffraction pattern substantially as given in Table 1, having characteristic peaks (expressed in degrees $2\theta$ (+/−0.2°$\theta$) at one or more of the following positions: 9.560, 16.040, 19.220, 19.720, 23.560, 24.440, 25.740, 29.020 and 29.100.

TABLE 1

| $2\theta$ | d-value | $I/I_0$ |
|---|---|---|
| 9.280 | 9.5220 | 2 |
| 9.560 | 9.2437 | 20 |
| 11.900 | 7.4308 | 2 |
| 13.140 | 6.7322 | 2 |
| 13.820 | 6.4025 | 2 |

TABLE 1-continued

| $2\theta$ | d-value | $I/I_0$ |
|---|---|---|
| 14.000 | 6.3205 | 2 |
| 14.400 | 6.1459 | 2 |
| 15.420 | 5.7415 | 2 |
| 15.980 | 5.5416 | 6 |
| 16.040 | 5.5210 | 8 |
| 16.980 | 5.2174 | 2 |
| 17.060 | 5.1931 | 3 |
| 18.480 | 4.7972 | 4 |
| 19.220 | 4.6141 | 100 |
| 19.660 | 4.5118 | 5 |
| 19.720 | 4.4982 | 7 |
| 21.160 | 4.1952 | 5 |
| 21.300 | 4.1680 | 4 |
| 23.000 | 3.8636 | 3 |
| 23.080 | 3.8504 | 3 |
| 23.200 | 3.8308 | 4 |
| 23.440 | 3.7921 | 4 |
| 23.560 | 3.7730 | 7 |
| 23.980 | 3.7079 | 2 |
| 24.440 | 3.6391 | 7 |
| 24.960 | 3.5645 | 2 |
| 25.360 | 3.5092 | 2 |
| 25.740 | 3.4582 | 11 |
| 27.280 | 3.2664 | 2 |
| 28.060 | 3.1773 | 4 |
| 28.180 | 3.1641 | 2 |
| 28.820 | 3.0953 | 2 |
| 29.020 | 3.0744 | 17 |
| 29.100 | 3.0661 | 10 |
| 29.620 | 3.0134 | 2 |
| 29.720 | 3.0035 | 6 |
| 30.240 | 2.9531 | 2 |

Form I of imidacloprid also exhibits a differential Scanning calorimetry (DSC) thermogram substantially as shown in FIG. 1. This thermogram is characterized by a predominant endotherm peak at about 145.7° C., as measured by Differential Scanning calorimeter at a scan rate of 10° C. per minute.

Form II of imidacloprid exhibits an X-ray powder diffraction pattern substantially as indicated in Table 2, having characteristic peaks (expressed in degrees $2\theta$ (+/−0.2°$\theta$) at one or more of the following positions: 4.580, 13.780, 15.000, 18.220, 18.420, 18.880 and 23.120.

TABLE 2

| $2\theta$ | d-value | $I/I_0$ |
|---|---|---|
| 4.580 | 19.2776 | 9 |
| 9.160 | 9.6465 | 1 |
| 9.320 | 9.4815 | 1 |
| 13.520 | 6.5438 | 1 |
| 13.780 | 6.4210 | 29 |
| 14.800 | 5.9806 | 2 |
| 15.000 | 5.9014 | 7 |
| 16.260 | 5.4468 | 1 |
| 16.440 | 5.3875 | 4 |
| 18.220 | 4.8650 | 6 |
| 18.420 | 4.8126 | 100 |
| 18.760 | 4.7262 | 3 |
| 18.880 | 4.6964 | 6 |
| 21.220 | 4.1835 | 0 |
| 22.080 | 4.0225 | 2 |
| 22.160 | 4.0081 | 1 |
| 22.840 | 3.8903 | 1 |
| 23.120 | 3.8438 | 7 |
| 23.300 | 3.8145 | 1 |
| 23.620 | 3.7636 | 2 |
| 26.180 | 3.4011 | 2 |
| 26.280 | 3.3884 | 1 |

TABLE 2-continued

| 2θ | d-value | I/I₀ |
|---|---|---|
| 29.540 | 3.0214 | 2 |
| 29.620 | 3.0134 | 2 |
| 29.960 | 2.9800 | 3 |
| 30.040 | 2.9723 | 3 |

Form II also exhibits a Differential Scanning calorimetry (DSC) thermogram substantially as shown in FIG. 2, which is characterized by a predominant endotherm peak at about 136.5° C., as measured by Differential Scanning calorimeter at a scan rate of 10° C. per minute.

A mixture of Form I and Form II of Imidacloprid also exhibits a Differential Scanning calorimetry (DSC) thermogram substantially as shown in FIG. 3, which is characterized by two predominant endotherm peaks at about 138.2° C. and 145.7° C., as measured by Differential Scanning calorimeter at a scan rate of 10° C. per minute.

Useful formulations of compounds containing both Form I and Form II can be prepared in conventional ways. These include preparation as dusts, pellets, solutions, suspensions, emulsions, wettable powders, emulsifiable concentrates, and the like. In particular, the compound containing both Form I and Form II may be formulated as solutions and suspensions. The inventor found that compared to Form I, Form II is easier to formulate into liquid formulations, like solutions, suspensions, emulsions and emulsifiable concentrate. While both forms can be difficult to formulate into agrochemically acceptable formulation, imidacloprid in Form I is especially difficult to formulate into liquid formulations because of gel formation.

During the manufacturing process, Form I is more readily made when imidacloprid is recrystallised in aqueous solution. Because Form I is so difficult to formulate into agrochemically acceptable formulations, if the Form I material obtained during recrystallisation cannot be converted to Form II, then it must be disposed of, resulting in lost revenue and inefficient production processes.

To date, there are no simple methods for controlling the crystallization of polymorphic forms of imidacloprid. There is thus an urgent and unmet need in the art for efficient method for selectively controlling the crystallization of polymorphic forms of imidacloprid.

SUMMARY

It has been found that embodiments disclosed herein satisfy this heretofore unmet need in that they provide a process for selectively controlling the crystallization of polymorphic forms of imidacloprid.

In another aspect, the embodiments disclosed herein provide a process for readily converting Form I polymorph into Form II polymorph.

In one aspect, there is provided a process for the preparation of a crystalline polymorph Form I of imidacloprid, comprising:

(1) dissolving imidacloprid in an appropriate amount of aqueous solvent or mixture of solvents to obtain an aqueous solution;

(2) cooling the aqueous solution slowly, thereby forming crystals of polymorph Form I of imidacloprid;

(3) isolating the crystals.

In another aspect, there is provided a process for the preparation of a crystalline polymorph Form II of imidacloprid, comprising:

(1) dissolving imidacloprid in an appropriate amount of non-aqueous solvent or mixture of non-aqueous solvents to obtain a non-aqueous solution;

(2) cooling the solution rapidly, thereby forming crystals of polymorph Form II of imidacloprid;

(3) isolating the crystals.

BRIEF DESCRIPTION OF DRAWINGS

Certain aspects of the embodiments described herein may be more clearly understood by reference to the drawings, which are intended to illustrate, but not limit, the invention, and wherein.

DETAILED DESCRIPTION OF SPECIFIC EMBODIMENTS

Figure 1:
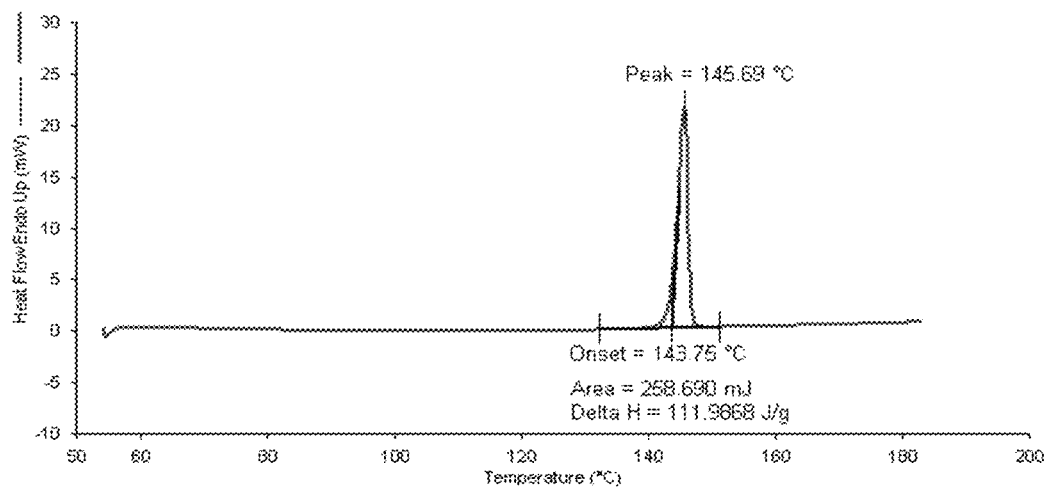
FIG. 1 is a graph of a thermogram obtained by DSC of a Form I polymorph of imidacloprid.

The crystallization methods described herein may be used to effect the formation of Form I, or Form II, or mixtures thereof, of imidacloprid. The presently disclosed crystallization methods allow for selectively controlling the crystallization of polymorphic forms of imidacloprid.

In one embodiment, Form I imidacloprid can be prepared by crystallizing imidacloprid from an aqueous solvent or mixture of solvents. The term "aqueous solvent or mixture of solvents" as used herein means water, or a mixture of water and one or more solvents selected from the group consisting of methanol, ethanol, tetrahydrofuran, acetonitrile, methylene chloride, isopropyl alcohol, acetone, N,N-dimethyl-Formamide, dimethyl sulfoxide, wherein when a mixture of water and solvent(s) is used, the weight ratio of water to solvent or solvent mixture is in the range of 99.9:1 to 1:9. Imidacloprid, or mixtures containing it, are dissolved with the aqueous solvent or mixture of solvents to obtain an aqueous solution of the imidacloprid dissolved in the aqueous solvent or mixture of solvents. The aqueous solution is then cooled slowly so as to form crystals of imidacloprid Form I, and then the crystals.

In a preferred embodiment, the process includes preparing an aqueous solution of the imidacloprid in one or more of the aforementioned aqueous solvent or mixture of solvents by applying heat until dissolution is complete, then cooling the aqueous solution slowly at a cooling rate of about 1° C./15-30 min until crystals appear, and then isolating the crystals.

In another embodiment, Form II imidacloprid can be prepared by crystallizing imidacloprid from a non-aqueous solvent or mixture of non-aqueous solvents. As used herein, the term "nonaqueous solvent or mixture of non-aqueous solvents" means one or more solvents selected from the group consisting of methanol, ethanol, tetrahydrofuran, acetonitrile, methylene chloride, isopropyl alcohol, acetone, N,N-dimethylformamide(DMF), dimethyl sulfoxide(DMSO), toluene, benzene, n-Hexane, petroleum ether, ethyl acetate, ether, dichloromethane, chloroform and carbon tetrachloride, in the absence of water. Imidacloprid, or mixtures containing it, are dissolved with the nonaqueous solvent or mixture of nonaqueous solvents to obtain a non-aqueous solution of the imidacloprid dissolved in the aqueous solvent or mixture of solvents. The nonaqueous solution is then cooled rapidly so as to form crystals of imidacloprid Form II, and then isolating the crystals.

In a preferred embodiment, the process includes preparing a non-aqueous solution of the imidacloprid in one or more of the aforementioned non-aqueous solvents by applying heat until dissolution is complete, cooling the non-aqueous solution rapidly at a cooling rate of about 1-2° C./min until crystals appear, and then isolating the crystals. Form I of imidacloprid.

In one embodiment is disclosed a method that provides the crystalline polymorphic form of imidacloprid designated Form I. This polymorph may be characterized by, for example, DSC or X-Ray powder diffraction.

For example, as shown in Table 1, Form I of imidacloprid exhibits an X-ray powder diffraction pattern having characteristic peaks (expressed in degrees 2θ+/−0.2°θ) at one or more of the following positions: 9.560, 16.040, 19.220, 19.720, 23.560, 24.440, 25.740, 29.020 and 29.110. The X-ray powder diffraction pattern can be determined using a Rigaku automated powder diffractometer—D/max-rB 12KW under the following conditions:

Copper(K-alpha1) radiation, 40 kv, 60 mA
C. Monochro: Monochromator (curved crystal)
Divergence slit: "1 deg"
Scattering slit: "1 deg"
Receiving slit: "0.15 mm"
Scan mode: continuous
Scan speed: 4.000 deg./min
Scan step: 0.020 deg
Scan axis: 2 Theta/Theta
Scan range: 2.5000→45.000 deg.

The samples were prepared by grinding using agate mortar and pestle. The obtained powder is then pressed into aluminum sample holder with rectangular cavity of 20 mm*15 mm and having a depth of 0.5 mm.

Furthermore, as shown in FIG. 1, Form I also exhibits a Differential Scanning calorimetry (DSC) thermogram which is characterized by a predominant endotherm peak at about 145.7° C., as measured by Differential Scanning calorimeter at a scan rate of 10° C. per minute.

In performing this measurement, weighted samples (2-4 mg) were purged with nitrogen flow during the measurements at a scan rate of 10° C. per minute. Aluminum standard pierced crucibles of 40 μL were used. The evaluation was performed using STAR software. As used herein, the term "about 145.7° C." means a range of 144° C. to 147° C. In this regard, it should be understood that the endotherm measured by a particular differential scanning calorimeter is dependent upon a number of factors, including the rate of heating (i.e. scan rate), the calibration standard utilized, instruments calibration, relative humidity, and the chemical purity of the sample being tested. Thus, an endotherm as measured by DSC on the instrument identified above may vary by as much as ±1.6° C.

In one embodiment, there are disclosed processes for preparing the imidacloprid polymorph Form I. Form I can be prepared by dissolving imidacloprid in an appropriate amount of aqueous solvent or mixture of aqueous solvents (i.e., an amount of solvent sufficient to dissolve the imidacloprid), heating this mixture to reflux temperature to achieve dissolution, and cooling the solution slowly to precipitate the product.

The imidacloprid starting material used for preparing Form I according to the disclosed process can be any form of imidacloprid including imidacloprid prepared in accordance with U.S. Pat. No. 6,307,053, amorphous imidacloprid, imidacloprid Form II, a mixture of imidacloprid Form I and Form II, or any other form of imidacloprid known in the art.

For example, in one embodiment, Form I of imidacloprid can be prepared by crystallizing imidacloprid from an aqueous solvent or a mixture of solvents selected from the group consisting of methanol, ethanol, tetrahydrofuran, acetonitrile, methylene chloride, isopropyl alcohol, acetone, N,N-dimethyl-Formamide, dimethyl sulfoxide; and isolating the resulting crystals. In a currently preferred embodiment, the process includes preparing an aqueous solution of imidacloprid in one or more of the aforementioned solvents, by applying heat to reflux temperature until dissolution is complete, and slowly cooling the solution to room temperature (defined herein as about 20° C. to about 25° C.). However, the solution can be slowly cooled to lower temperatures, for example 0° C.-5° C. The crystals are then isolated by any conventional method known in the art, for example by filtration, centrifugation, etc. Form II of imidacloprid In another embodiment is disclosed a method that provides the crystalline polymorphic form of imidacloprid designated Form II. This polymorph may be characterized by, for example, by DSC or X-ray powder diffraction spectrometry.

For example, as shown in Table 2, Form II of imidacloprid exhibits an X-ray powder diffraction pattern having characteristic peaks (expressed in degrees 2θ+/−0.2°θ) at one or more of the following positions: 4.580, 13.780, 18.420, 18.880 and 23.120. The X-Ray powder diffraction was measured as described above.

Figure 2:
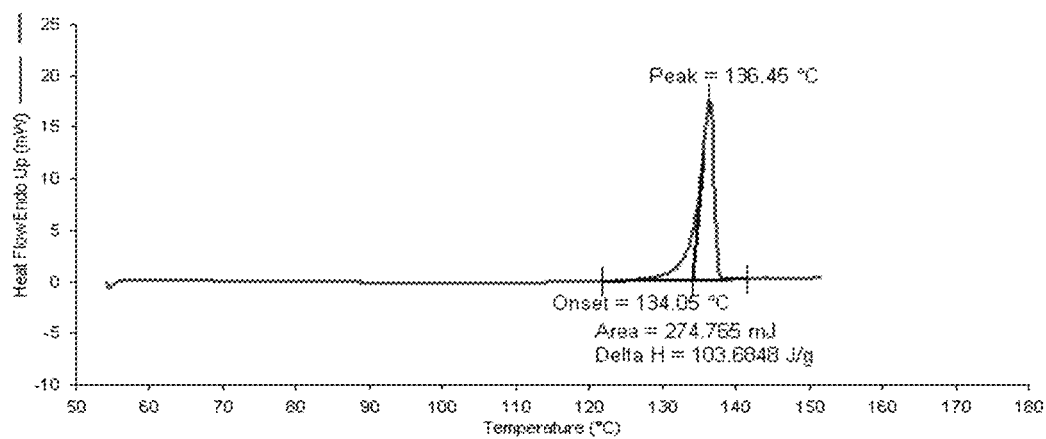
FIG. 2 is a graph of a thermogram obtained by DSC of a Form II polymorph of imidacloprid.
Figure 3:
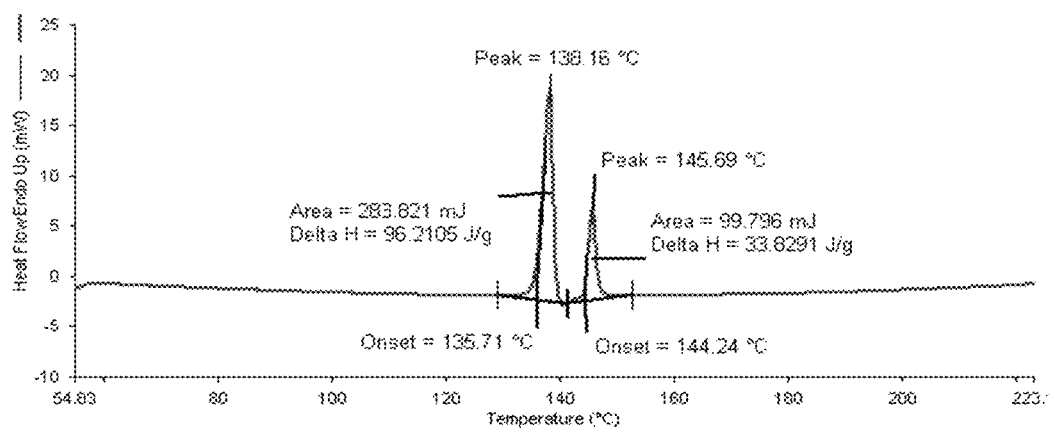
FIG. 3 is a graph of a thermogram obtained by DSC of a mixture of a Form I polymorph of imidacloprid and a Form II polymorph of imidacloprid.

Furthermore, as shown in FIG. 2, Form II also exhibits a Differential Scanning calorimetry (DSC) thermogram which is characterized by a predominant endotherm peak at about 136.5° C., as measured by Differential Scanning calorimeter at a scan rate of 10° C. per minute. As used herein, the term "about 136.5° C." means from about 135° C. to about 138° C. Thus, an endotherm as measured by DSC on the instrument identified above may vary by as much as ±1.5° C.

In another embodiment are disclosed processes for preparing the imidacloprid polymorph Form II. Form II can be prepared by dissolving imidacloprid in an appropriate amount of non-aqueous solvent or mixture of nonaqueous solvents selected from the group consisting of methanol, ethanol, tetrahydrofuran, acetonitrile, methylene chloride, isopropyl alcohol, acetone, N,N-dimethyl-Formamide (DMF), dimethyl sulfoxide(DMSO), toluene, benzene, n-Hexane, petroleum ether, ethyl acetate, ether, dichloromethane, chloroform, and carbon tetrachloride to obtain a non-aqueous solution.

In a currently preferred embodiment, the process includes preparing a non-aqueous solution of imidacloprid in one or more of the aforementioned solvents by applying heat to reflux temperature until dissolution is complete, and rapidly cooling the solution to room temperature (i.e., in 15-30 minutes). Room temperature is defined herein as about 20° C. to about 25° C. However, the solution can be rapidly cooled to lower temperature, for example 0° C.-5° C. at a cooling rate of about 1-2° C./mini. The crystals are then isolated by any conventional method known in the art, for example by filtration, centrifugation, etc.

The imidacloprid starting material used for preparing Form II can be any form of imidacloprid including imidacloprid prepared in accordance with U.S. Pat. No. 6,307,053, amorphous imidacloprid, imidacloprid Form II, a mixture of imidacloprid Form I and Form II, or any other form of imidacloprid known in the art.

The invention will now be described further by reference to the following examples, which are intended to illustrate, but not limit, the scope of the appended claims.

EXAMPLE 1

Synthesis of Imidacloprid 7.8 g (60 mmol) of 2-nitroiminoimidazolidine and 12.1 g (87.5 mmol) of potassium carbonate were dissolved in 60 ml of acetonitrile in a reflux flask. The mixture is heated to a temperature sufficient for achieving reflux operating condition. 8.1 g (50.0 mole) of 2-chloro-5-chloromethyl pyridine is dissolved in 40 ml of acetonitrile, and is dropwisely and continuously added into the flask under the reflux condition for a period of 0.5 hr, i.e. the addition rate is about 1.5 ml/minute (the addition rate at the onset of the reaction corresponds to 0.0278 equivalent of 2-chloro-5-chloromethyl pyridine per equivalent of 2-nitroiminoimidazolidine per minute) After completion of the reaction, the mixture is subjected to filtration. The filtrate is concentrated, and is further purified.

EXAMPLE 2

Preparation of Imidacloprid Form I 2 g of imidacloprid prepared according to Example 1 were heated in 10 ml of a mixture of methanol and water to reflux temperature (ratio of methanol:water=1:1) until complete dissolution of the imidacloprid was observed. The solution was then slowly cooled to 0-5° C. at a cooling rate of about 1° C./15-30 min and crystals were formed from the solution. The crystals were filtered out and dried at 40-50° C. in an oven. The crystals were characterized as imidacloprid Form I using X-ray powder diffraction and DSC.

EXAMPLE 3

Preparation of Imidacloprid Form I 2 g of imidacloprid prepared according to Example 1 were heated in 10 ml of a mixture of methanol and water (ratio of methanol:water=1:2) to reflux temperature until complete dissolution of the imidacloprid was observed. The solution was then slowly cooled to 0-5° C. at a cooling rate of about 1° C./15-30 min and crystals were formed from the solution. The crystals were filtered out and dried at 40-50° C. in an oven. The crystals were characterized as imidacloprid Form I using X-ray powder diffraction and DSC.

EXAMPLE 4

Preparation of Imidacloprid Form I 2 g of imidacloprid prepared according to Example 1 were heated in 10 ml of a mixture of DMF and water (DMF:water=9:1) to reflux temperature until complete dissolution of the imidacloprid was observed. The solution was then slowly cooled to 20-25° C. at a cooling rate of about 1° C./15-30 min and crystals were formed from the solution. The crystals were filtered out and dried at 40-50° C. in an oven. The crystals were characterized as Imidacloprid Form I using X-ray powder diffraction and DSC.

EXAMPLE 5

Preparation of Imidacloprid Form II 2 g of imidacloprid prepared according to Example 1 were heated in 10 ml of methanol to reflux temperature until complete dissolution of the imidacloprid was observed. The solution was then rapidly cooled to 0-5° C. at a cooling rate of about 1-2° C./min and crystals were formed from the solution. The crystals were filtered out and dried at 40-50° C. in an oven. The crystals were characterized as imidacloprid Form II using X-ray powder diffraction and DSC.

EXAMPLE 6

Preparation of Imidacloprid Form II 2 g of imidacloprid prepared according to Example 1 were heated in 10 ml of methylene chloride to reflux temperature until complete dissolution of the imidacloprid was observed. The solution was then rapidly cooled to 0-5° C. at a cooling rate of about 1-2° C./min and crystals were formed from the solution. The crystals were filtered out and dried at 40-50° C. in an oven. The crystals were characterized as imidacloprid Form II using X-ray powder diffraction and DSC.

EXAMPLE 7

Preparation of Imidacloprid Form II 2 g of imidacloprid Form I prepared according to Examples 2-4 were heated in 10 ml of methanol to reflux temperature until complete dissolution of the imidacloprid was observed. The solution was then rapidly cooled to 0-5° C. at a cooling rate of about 1-2° C./min and crystals were formed from the solution. The crystals were filtered out and dried at 40-50° C. in an oven. The crystals were characterized as imidacloprid Form II using X-ray powder diffraction and DSC.

EXAMPLE 8

Preparation of Imidacloprid Form II 2 g of of a mixture Form I and Form II imidacloprid prepared according to Example 1 were heated in 10 ml of methanol to reflux temperature until complete dissolution of the imidacloprid was observed. The solution was then rapidly cooled to 0-5° C. at a cooling rate of about 1-2° C./min and crystals were formed from the solution. The crystals were filtered out and dried at 40-50° C. in an oven. The crystals were characterized as Imidacloprid Form II using X-ray powder diffraction and DSC.

The invention having been described by reference to certain specific embodiments and examples, it will be understood that these specific embodiments and examples are intended to illustrate the invention, and not to limit the scope of the appended claims.

The invention claimed is:

1. A process for the preparation of a Form II crystalline polymorph of imidacloprid exhibiting an X-ray powder diffraction pattern having characteristic peaks (expressed in degrees $2\theta+/-0.2°\theta$) at one or more of the following positions: 4.580, 13.780, 18.420, 18.880 and 23.120, or exhibiting a Differential Scanning calorimetry (DSC) thermogram which is characterized by a predominant endotherm peak at about 136.5° C., or both, comprising:

(i) dissolving imidacloprid in an amount of non-aqueous solvent or mixture of non-aqueous solvents appropriate to obtain a non-aqueous solution, wherein the non-aqueous solvent is selected from the group consisting of methanol, ethanol, tetrahydrofuran, acetonitrile, methylene chloride, isopropyl alcohol, acetone, N,N-dimethyl-formamide, dimethyl sulfoxide, toluene, benzene, n-hexane, petroleum ether, ethyl acetate, ether, dichloromethane, chloroform, and carbon tetrachloride;

(ii) cooling the solution rapidly, thereby forming crystals of polymorph Form II of imidacloprid;

(iii) isolating the crystals.

2. The process according to claim 1, wherein step (i) comprises heating the imidacloprid or the non-aqueous solvent or mixture of solvents, or both.

3. The process according to claim 2, wherein in step (ii), the solution is cooled rapidly from a temperature above room temperature to room temperature.

4. The process according to claim 2, wherein in step (ii), the solution is cooled rapidly from a temperature above room temperature to room temperature in 15-30 minutes.

5. The process according to claim 2, wherein in step (ii), the solution is cooled rapidly to a temperature of 0-5° C.

6. The process according to claim 2, wherein in step (ii), the solution is cooled rapidly to a temperature of 0-5° C. in 15-30 minutes.

7. The process according to claim 2, wherein in step (i), the non-aqueous solvent is selected from the group consisting of methanol, and methylene chloride.

8. The process according to claim 2, wherein the imidacloprid dissolved in the non-aqueous solvent or mixture of solvents comprises Form I polymorph of imidacloprid, or a mixture of Form I and Form II polymorphs of imidacloprid.

* * * * *